US00PP31416P2

(12) United States Plant Patent
Van Dijk

(10) Patent No.: US PP31,416 P2
(45) Date of Patent: Jan. 28, 2020

(54) ***ANTHURIUM* PLANT NAMED 'ANTHOSZMO'**

(50) Latin Name: ***Anthurium andraeanum* L.**
Varietal Denomination: ANTHOSZMO

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/350,621

(22) Filed: Dec. 11, 2018

(51) Int. Cl.
*A01H 5/02* (2018.01)
*A01H 6/00* (2018.01)

(52) U.S. Cl.
USPC ..... Plt./367

(58) Field of Classification Search
USPC ..... Plt./365, 367
See application file for complete search history.

(56) References Cited

PUBLICATIONS

UPOV-PLUTO : Plant Variety Database, citation for 'ANTHOSZMO' (1 page).*
EU Community Plant Variety Rights Application No. 2016/2944, Application n°A201603029, filed Nov. 25, 2016, 8 pages.
EU Community Plant Variety Office Official Gazette, Jan. 2017, Feb. 15, 2017, cover page and pp. 30, 51.
EU Community Plant Variety Rights Certificate on the Grant, EU 49808, Jul. 2, 2018, 2 pages.
EU Community Plant Variety Office Official Gazette, May 2018, Oct. 15, 2018, cover page and p. 73.

* cited by examiner

*Primary Examiner* — Susan McCormick Ewoldt
(74) *Attorney, Agent, or Firm* — Jondle & Associates, P.C.

(57) ABSTRACT

A new *Anthurium* plant named 'ANTHOSZMO' particularly distinguished by having shiny, pink, ovate and durable spathes that retain the original color for a very long period of time, pink spadices with orange-light green tips, dark green and deltoid, durable leaves, early and rich flowering continuously throughout the year, and a plant height of 24.0 cm to 29.0 cm is disclosed.

3 Drawing Sheets

Genus and species: *Anthurium andraeanum* L.
Variety denomination: 'ANTHOSZMO'.

BACKGROUND OF THE NEW PLANT

The present invention comprises a new and distinct variety of *Anthurium*, botanically known as *Anthurium andraeanum* L., and hereinafter referred to by the variety name 'ANTHOSZMO'. The new *Anthurium* plant is a product of a planned breeding program conducted by the inventor in Bleiswijk, the Netherlands. The objective of this breeding program was to create a new 24.0 cm to 29.0 cm height plant with shiny, pink, ovate and durable spathes.

The new variety originated from a cross-pollination made in December 2001 in Bleiswijk, The Netherlands. The female parent was a red *Anthurium* pot plant designated 'ANTHEPEDI' (U.S. Plant Pat. No. 18,644), and the male parent was a white *Anthurium* pot plant designated '3644-01' (unpatented).

Asexual reproduction of the new variety by tissue culture in 2014 in Bleiswijk, The Netherlands, has demonstrated that the new variety reproduces true to type with all of the characteristics, as herein described, firmly fixed and retained through successive generations.

Plant Breeder's Rights for this variety have been applied for in the European Union on Nov. 25, 2016. 'ANTHOSZMO' has not been made publicly available or sold anywhere in the world more than one year prior to the effective filing date of this application.

SUMMARY OF THE INVENTION

The following are the most outstanding and distinguishing characteristics of this new variety when grown under normal horticultural practices in Bleiswijk, The Netherlands:

1) Shiny, pink, ovate spathes;
2) Pink spadices with orange-light green tips; and
3) Green, deltoid leaves.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 28-week old plant grown in a greenhouse in Bleiswijk, The Netherlands, in October 2018. Colors in the photographs may differ from the color values cited in the detailed botanical description, which accurately describe the actual colors of the new variety.

DESCRIPTION OF THE NEW VARIETY

Figure 1:
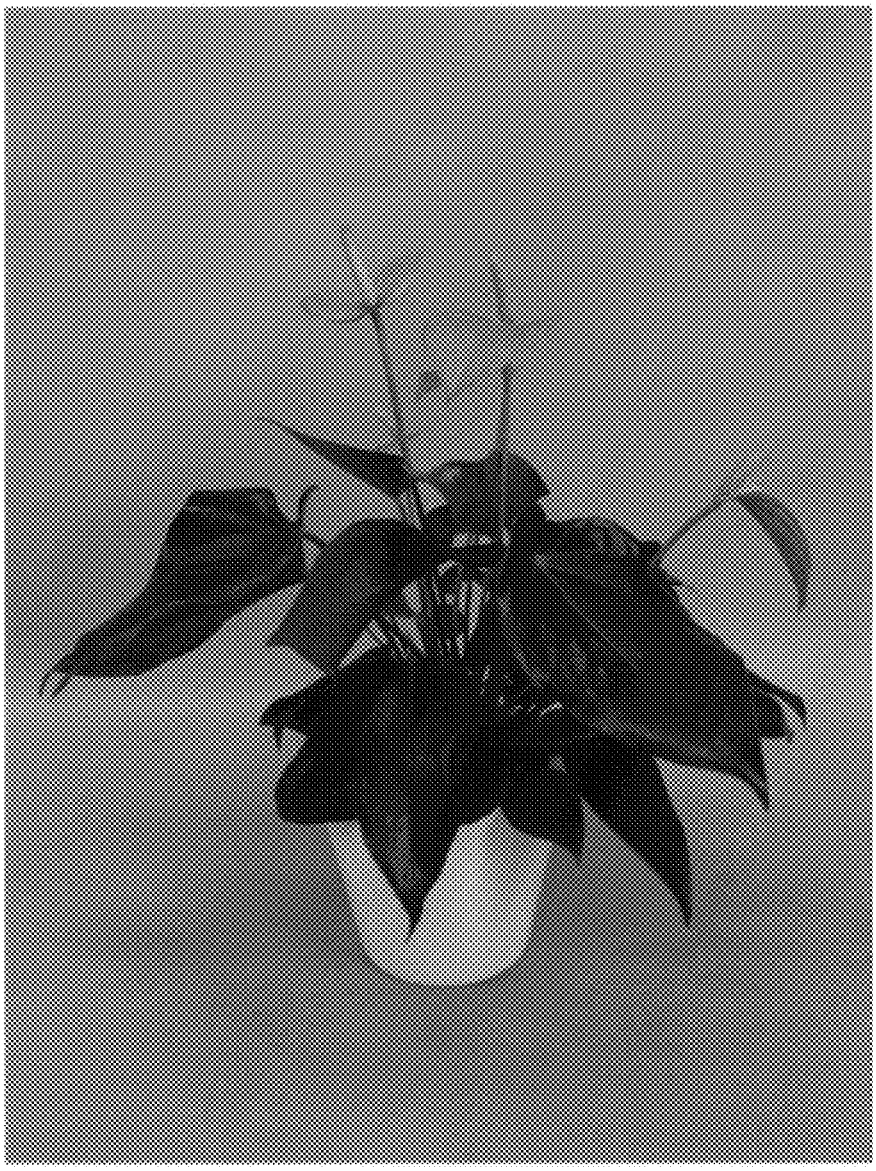
FIG. 1 shows the overall plant habit, including blooms and foliage.
Figure 2:
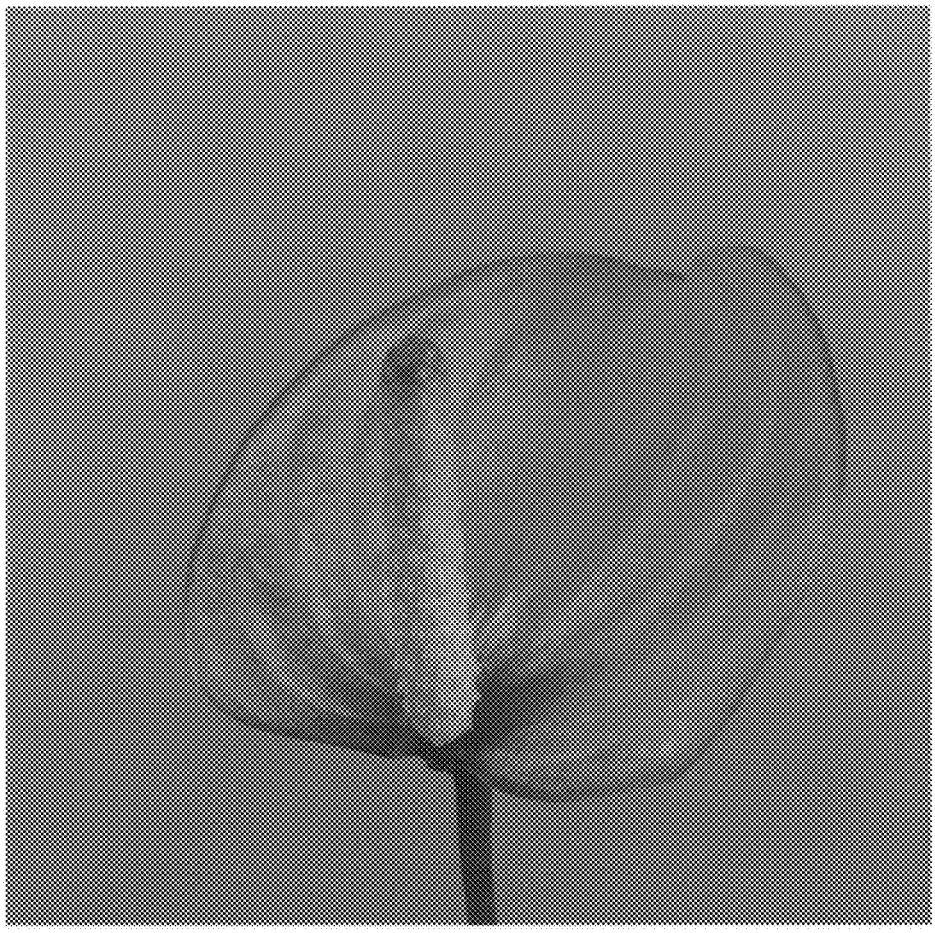
FIG. 2 shows a close-up of the mature spathe.
Figure 3:
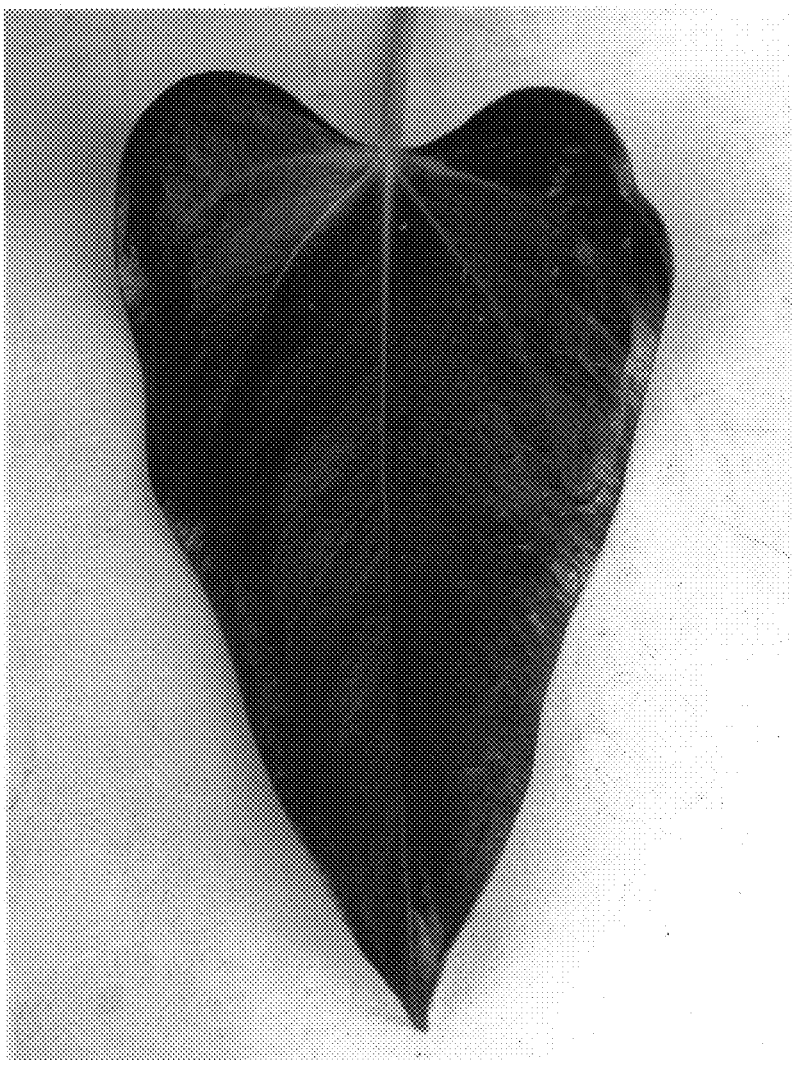
FIG. 3 shows a close-up of the upper leaf blade surface.

The following detailed description sets forth the distinctive characteristics of 'ANTHOSZMO'. The data which define these characteristics were collected from asexual reproductions carried out in Bleiswijk, The Netherlands. The plant history was taken on 28-week old plants which were planted from tissue culture in 9 centimeter (diameter) pots and grown in a glass greenhouse between 19° C. and 24° C. Observations were made in October 2018. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andraeanum* L.

*Common name*.—*Anthurium*.

*Denomination*.—'ANTHOSZMO'.

Parentage:

*Female parent*.—*Anthurium* plant 'ANTHEPEDI' (U.S. Plant Pat. No. 18,644).

*Male parent*.—*Anthurium* plant '3644-01' (unpatented).

Plant:

*Propagation*.—Tissue culture.

*Root description*.—Fleshy, light yellow colored roots with small hairy lateral roots having yellow colored root tips.

*Time to produce a finished flowering plant*.—26 to 30 weeks after planting in a 9 cm (diameter) pot.

*Growth habit*.—Upright.

*Height* (*measured from soil, including inflorescence*).—24.0 cm to 29.0 cm.

*Width* (*measured from leaf tips*).—28.0 cm to 32.0 cm.

Leaves:

*Immature leaves*.—Length: 11.0 cm to 13.0 cm. Width: 7.0 cm to 8.0 cm. Color: Upper surface: RHS 146A. Lower surface: RHS 146B. Texture (both upper and lower surfaces): Shiny, soft and smooth.

*Mature leaves*.—Length (fully expanded): 14.0 cm to 16.0 cm. Width: 8.5 cm to 9.5 cm. Shape: Deltoid. Apex: Acuminate. Base: Cordate. Leaf blade angle with the petiole: Between 125 degrees and 145 degrees. Leaf margin: Entire. Color: Upper surface: RHS 147A. Lower surface: RHS 146A. Texture (both upper and lower surfaces): Shiny, leathery and thick. Venation: Pinnate veining; the mid-vein and primary veins (the veins that radiate out from the junction of petiole and leaf) protrude at the underside of the leaf blade. Venation color: Upper surface: RHS 144B. Lower surface: RHS 144C.

*Lobes*.—Present. Arrangement: Leaf blade has two lobes extending past the petiole. The lobes are non-touching. Length of lobes of mature leaf blades: 0.5 cm to 1.5 cm. Width of lobes of mature leaf blades: 2.0 cm to 3.0 cm. Distance from petiole/leaf junction to highest point on lobes of mature leaf: 1.5 cm to 2.5 cm.

*Petiole*.—Cross-section: Round. Diameter: 0.2 cm to 0.3 cm. Length: 8.0 cm to 11.0 cm for a mature leaf size. Color: Mature leaf: RHS 144A. Immature leaf: RHS 144B. Cataphyll color surrounding the petiole: Outside: RHS 145A. Inside: RHS 145B.

*Geniculum*.—Length: 2.0 cm to 2.5 cm. Width: 0.3 cm to 0.4 cm. Color: RHS 144A.

Inflorescence:

*Arrangement*.—Single.

*Flowering habit* (*length of flowering season*).—Continuous.

*Number of inflorescences per plant*.—6 to 8.

*Fragrance*.—Absent.

*Longevity of inflorescence on plant*.—Over a year.

Spathe:

*Buds*.—The spathe is tightly rolled around the spadix and extrudes from the peduncle sheath. After the spathe is fully open, the peduncle elongates some extra centimeters (2.0 cm to 4.0 cm).

*Arrangement*.—Spathe angle with the peduncle is between 80 degrees and 100 degrees; the spathe stands on a wiry peduncle about 7.0 cm to 9.0 cm above the foliage.

*Shape*.—Ovate.

*Apex*.—Abruptly acuminate.

*Base*.—Cordate.

*Texture*.—Shiny.

*Margin*.—Undulated.

*Size*.—Length: 8.0 cm to 8.5 cm. Width: 6.5 cm to 7.0 cm.

*Lobes*.—Absent.

*Color*.—Just fully open: Upper surface: RHS 50B. Lower surface: RHS 50C/D. This pink color remains for a very long period, at least more than 30 weeks after opening.

Peduncle:

*Shape*.—Erect.

*Cross-section*.—Round.

*Length*.—20.0 cm to 24.0 cm.

*Diameter*.—0.2 cm to 0.3 cm.

*Color*.—RHS 144B.

Flowering time:

*General*.—One small, rooted, untreated tissue culture plant of 8.0 cm tall will flower, depending on the season, after 26 to 28 weeks and 6 to 7 blossoms appear. More blossoms appear after some additional weeks so that a full flowering and commercial plant will have 7 to 8 pink spathes. Smaller blossoms may occur on immature plants.

Spadix:

*Size*.—Length: 3.0 cm to 4.0 cm (depending on flower size). Width (at apex): 0.4 cm to 0.5 cm. Width (at base): 0.5 cm to 0.6 cm.

*Shape*.—Columnar.

*Angle from spadix tip to peduncle*.—160 degrees to 170 degrees.

*Texture*.—When the spathe is unfurling the spadix is smooth. When the spadix matures, small stigmata protrude. The stigmata are evenly distributed around the spadix. The spadix matures from base to top, slowly giving the spadix a somewhat rough appearance.

*Color*.—Immature: RHS 26A and 152B. Mature: RHS 51D. Ages to: RHS N144A.

Flowers:

*Quantity per spadix*.—100 to 150.

*Spadix flower arrangement*.—Bisexual, rounded in cross-section.

*Shape*.—Rounded.

*Size*.—Length: 0.05 cm to 0.10 cm. Diameter (maximum): 0.10 cm.

*Color*.—RHS 182C.

Reproductive organs:

*Stamens*.—Not visible.

*Pollen amount*.—Absent.

*Pistil*.—Quantity: 100 to 150. Length: Less than 0.01 cm. Color: RHS 182C.

*Style*.—Not observed to date.

*Stigma*.—Shape: Ovoid. Diameter: Less than 0.01 cm. Color: RHS 182C.

*Ovary*.—Rarely visible.

*Ovary color*.—Not measured.

Fruit and seed set: None observed to date.

Disease and pest resistance: Resistance to diseases and pests common to *Anthurium* has not been observed to date.

COMPARISON WITH PARENTAL AND SIMILAR COMMERCIAL VARIETIES

'ANTHOSZMO' differs from the female parent plant 'ANTHEPEDI' (U.S. Plant Pat. No. 18,644) in that 'ANTHOSZMO' has spathes that are pink, spadices that are RHS 51D at the base and RHS 152B and 26A at the tip, and cataphylls that are green on the outside, whereas 'ANTHEPEDI' has spathes that are red, spadices that are RHS 155B at the base and RHS 153D at the tip, and cataphylls that are light green on the outside with a bit of red at the tip.

'ANTHOSZMO' differs from the male parent plant '3644-01' (unpatented) in that 'ANTHOSZMO' has spathes that are pink and spadices that are RHS 51D at the base and RHS 152B and 26A at the tip, whereas '3644-01' has spathes that are white and spadices that are RHS 158B at the base and RHS 10C and 150C at the tip.

'ANTHOSZMO' differs from similar commercial variety 'ANTHDINWAQ' (U.S. Plant Pat. No. 26,048) in that 'ANTHOSZMO' has abruptly acuminate spathe apexes and deltoid leaves, whereas 'ANTHDINWAQ' has acute spathe apexes and ovate leaves. Additionally, 'ANTHOSZMO' has longer spathes than 'ANTHDINWAQ'.

'ANTHOSZMO' differs from similar commercial variety 'ANTHDATAM' (U.S. Plant Pat. No. 27,699) in that 'ANTHOSZMO' has ovate spathes with abruptly acuminate apexes and deltoid leaves, whereas 'ANTHDATAM' has cordate spathes with mucronate apexes and ovate-cordate leaves.

I claim:

1. A new and distinct variety of *Anthurium* plant named 'ANTHOSZMO', substantially as illustrated and described herein.

* * * * *